United States Patent [19]

Geisberg

[11] Patent Number: 6,103,536
[45] Date of Patent: Aug. 15, 2000

[54] INTERNALLY REFERENCED COMPETITIVE ASSAYS

[75] Inventor: Mark S. Geisberg, Los Angeles, Calif.

[73] Assignee: Silver Lake Research Corporation, Monrovia, Calif.

[21] Appl. No.: 09/071,183

[22] Filed: May 1, 1998

Related U.S. Application Data

[60] Provisional application No. 60/090,104, May 2, 1997, abandoned.

[51] Int. Cl.[7] ........................ G01N 33/543; G01N 33/558; G01N 33/532; C12Q 1/00; C12Q 1/54
[52] U.S. Cl. ..................... 436/518; 436/514; 436/517; 436/523; 436/526; 436/531; 436/533; 436/544; 436/545; 436/546; 422/50; 422/55; 422/57; 422/68.1; 422/69; 422/70; 422/82.05; 435/4; 435/7.1; 435/7.5; 435/7.92; 435/7.93; 435/14; 435/25; 435/28; 435/287.1; 435/287.2; 435/288.7; 435/287.9
[58] Field of Search ..................... 436/514, 517, 436/518, 523, 526, 531, 533, 544–546, 164, 169, 800, 804, 805, 829; 422/50, 55–57, 68.1, 69, 70, 82.05; 435/4, 7.1, 7.5, 7.92, 7.93, 14, 25, 28, 287.1, 287.2, 287.7, 288.7, 287.9

[56] References Cited

U.S. PATENT DOCUMENTS

| | | |
|---|---|---|
| 3,646,346 | 2/1972 | Catt . |
| 3,857,931 | 12/1974 | Hager . |
| 3,966,345 | 6/1976 | Ullman et al. . |
| 4,062,733 | 12/1977 | Edwards et al. . |
| 4,104,029 | 8/1978 | Maier . |
| 4,181,636 | 1/1980 | Fischer . |
| 4,235,960 | 11/1980 | Sasse et al. ................... 435/7 |
| 4,264,327 | 4/1981 | Blum ........................... 23/230 |
| 4,264,766 | 4/1981 | Fischer . |
| 4,313,734 | 2/1982 | Leuvering et al. . |
| 4,366,241 | 12/1982 | Tom et al. . |
| 4,373,932 | 2/1983 | Gribnau et al. . |
| 4,376,110 | 3/1983 | David et al. . |
| 4,429,050 | 1/1984 | Yasuda et al. ................ 436/538 |
| 4,548,908 | 10/1985 | Kameda ....................... 436/500 |
| 4,650,770 | 3/1987 | Liu et al. ...................... 436/523 |

(List continued on next page.)

FOREIGN PATENT DOCUMENTS

| | | |
|---|---|---|
| 296 724 B1 | 6/1988 | European Pat. Off. . |
| 323 605 B1 | 1/1994 | European Pat. Off. . |
| 291 194 B1 | 2/1994 | European Pat. Off. . |
| WO 92/12428 | 7/1992 | WIPO . |
| WO 94/01774 | 1/1994 | WIPO . |

OTHER PUBLICATIONS

Bangs, "Latex Immunoassays," *J. Clin. Immunoassay*, 13:127–131 (1980).
Cantarero et al., "The Absorption Characteristics of Proteins for Polystyrene and Their Significance in Solid phase Immunoassays," *Analytical Biochemistry*, 105:375–382 (1980).
Cutrecasas, *J. Bio. Chem.*, 245:3059 (1970).
Kennedy et al., *Clin. Chem Acta*, 70:1 (1976).
March et al., *Anal. Biochem*, 60:149, et seq. (1974).

*Primary Examiner*—Christopher L. Chin
*Assistant Examiner*—Pensee T. Do
*Attorney, Agent, or Firm*—Nutter, McClennen & Fish LLP; Thomas J. Engellenner; Scott D. Rothenberger

[57] ABSTRACT

The present invention provides internally calibrated competitive assays for use on a solid support. Additionally, the invention provides a method of using such assays.

13 Claims, 6 Drawing Sheets

U.S. PATENT DOCUMENTS

| | | |
|---|---|---|
| 4,703,017 | 10/1987 | Campbell et al. . |
| 4,740,468 | 4/1988 | Weng et al. . |
| 4,775,636 | 10/1988 | Moremans et al. . |
| 4,803,170 | 2/1989 | Stanton et al. ............... 436/518 |
| 4,837,168 | 6/1989 | de Jaeger et al. . |
| 4,843,000 | 6/1989 | Litman et al. . |
| 4,849,338 | 7/1989 | Litman et al. . |
| 4,861,711 | 8/1989 | Friesen et al. . |
| 4,868,131 | 9/1989 | Hiratsuka ...................... 436/528 |
| 4,916,056 | 4/1990 | Brown, III et al. . |
| 4,954,452 | 9/1990 | Yost et al. . |
| 5,045,479 | 9/1991 | Newman et al. ............... 435/518 |
| 5,141,875 | 8/1992 | Kelton et al. . |
| 5,252,459 | 10/1993 | Tarcha et al. . |
| 5,514,558 | 5/1996 | Ceriani et al. ................. 435/7.92 |
| 5,559,041 | 9/1996 | Kang et al. . |
| 5,589,344 | 12/1996 | Contestable et al. .......... 435/7.9 |
| 5,591,645 | 1/1997 | Rosenstein et al. . |
| 5,648,274 | 7/1997 | Chandler ........................ 436/514 |
| 5,780,251 | 7/1998 | Klainer et al. ................. 435/7.93 |
| 5,824,476 | 10/1998 | Wallace ........................... 435/6 |
| 5,879,881 | 3/1999 | Rubenstein ..................... 435/5 |
| 5,895,750 | 4/1999 | Mushahwar et al. .......... 435/7.5 |
| 5,922,615 | 7/1999 | Nowakowski et al. ........ 436/518 |
| 5,928,862 | 7/1999 | Morrison ........................ 435/6 |
| 5,939,331 | 8/1999 | Burd et al. ..................... 436/518 |
| 5,981,298 | 11/1999 | Chudzik et al. ................ 436/514 |
| 5,989,921 | 11/1999 | Charlton et al. ............... 436/501 |
| 6,001,658 | 12/1999 | Fredrickson ................... 436/514 |

INTERNALLY REFERENCED COMPETITIVE ASSAYS

This application claims the benefit of U.S. Provisional Application No. 60/090,104, filed May 2, 1997, now abandoned which was converted from Application Ser. No. 08/850,153 and is incorporated herein by reference.

BACKGROUND INFORMATION

Ligand-receptor assays utilize the exquisite specificity and sensitivity of bioreagents to identify and quantify minute amounts of a wide range of substances also referred to as analytes. Competitive ligand-receptor assays are one variant of ligand-receptor assays in general. In competitive ligand-receptor assays, analyte substances in the sample compete with a signal-producing substance for a limited number of binding sites on the counterpart of the ligand-receptor pair. After the binding has taken place, the amount of signal-producing substance bound to the counterpart is detected by several different means. The signal intensity of competitive ligand-receptor assay is in an inverse relationship with the concentration of analyte present; thus, a sample with no analyte will give a maximum signal intensity, and a sample with a range of analyte concentration will produce less than a maximum signal. Competitive ligand-receptor assays can be adapted to many different types of signal-producing systems: enzymes, radioisotopes, fluorescent compounds, colored latex particles, and the like. The signal-producing means, however, does not alter the inverse relationship between signal intensity and analyte concentration (FIG. 1). Conventional competitive ligand-receptor assays to date have several disadvantages. First, such an assay has its maximum sensitivity in a narrow analyte concentration range, around the inflection point of the signal intensity versus analyte concentration curve (FIG. 1). This sensitivity parameter, defined as the change in signal intensity per unit change in analyte concentration ($\Delta$signal/$A\Delta$[analyte]), decreases significantly as the analyte concentration is farther from the inflection point of the curve. The maximum sensitivity of the assay is at the concentration which gives 50% of the maximum signal intensity. Furthermore, changing the maximum sensitivity range of a competitive assay has to date proven very difficult. Changing such a range requires careful experimentation as to the new amounts of reagents supplied for the assay, as well as a careful recalibration with an external source.

Yet another major disadvantage of competitive ligand-receptor assays is the absolute need for calibration. This disadvantage manifests itself in so-called semi-quantitative assays, where a "yes" or "no" is indicated by the assay based on the presence or absence of a predetermined concentration of analyte. Such semi-quantitative competitive ligand-receptor assays are difficult to perform without external calibration, thus limiting their usefulness in a variety of important market segments. Due to the inverse relationship between signal intensity and analyte concentration, all but the most concentrated samples will give a signal in the assay, and therefore a standard curve (or at least one control point with a known standard) must be run in parallel with the sample assay to interpret accurately any reading of the sample assay. For example, an optical density reading of 0.5 in a competitive immunoassay using enzymes as a signal producing system is meaningless. However, if the user runs a known standard of, for example, 10 micrograms per milliliter of analyte and obtains a reading of 1.0, then the sample with the reading of 0.5 can be said to be more concentrated than the 10 microgram per milliliter sample.

The need for standardization has severely limited the practical usefulness of current competitive ligand-receptor assays by requiring several runs of the assay to determine one sample concentration. One of the major disadvantages of the requirement for outside calibration is the concomitant reduction of precision and accuracy of each assay due to inter-assay variability in the calibration process. Furthermore, while there are commercially-available immunochromatographic test strip versions of the ligand-receptor competitive assay available that do not require external calibration, these assays are designed to give a positive indication for the analyte at the least sensitive portion of the analyte concentration versus signal intensity curve. Thus, these immunochromatographic test strips are to be interpreted as positive for analyte in the sample when no signal is seen at the test line. This signal intensity would correspond to the highest concentration range in the dose response curve set forth in FIG. 1. As one skilled in the art would recognize, the precision of the determination of analyte concentration is compromised in such an assay.

Thus, there exists a need for a competitive assay which retains the advantages of ligand-receptor tests (i.e., both specificity and sensitivity) for minute amounts of analyte, while improving the ratio of $\Delta$signal/$\Delta$[analyte] in a wide range of analyte concentrations. Furthermore, a need exists for such an assay where the operator does not have to use an external calibration. As an extension for this need, there exists a need for competitive ligand-receptor assays wherein the maximum of sensitivity can be easily shifted and a semi-quantitative assay with great precision is available without the need for external calibration. The present invention provides these advantages and more.

SUMMARY OF THE INVENTION

The present invention is directed to a device for the detection of at least one analyte in a solution, as discussed below. Furthermore, the present invention is directed to a method of using such a device for the detection of at least one analyte in solution as discussed below.

DETAILED DESCRIPTION OF INVENTION

Figure 1:
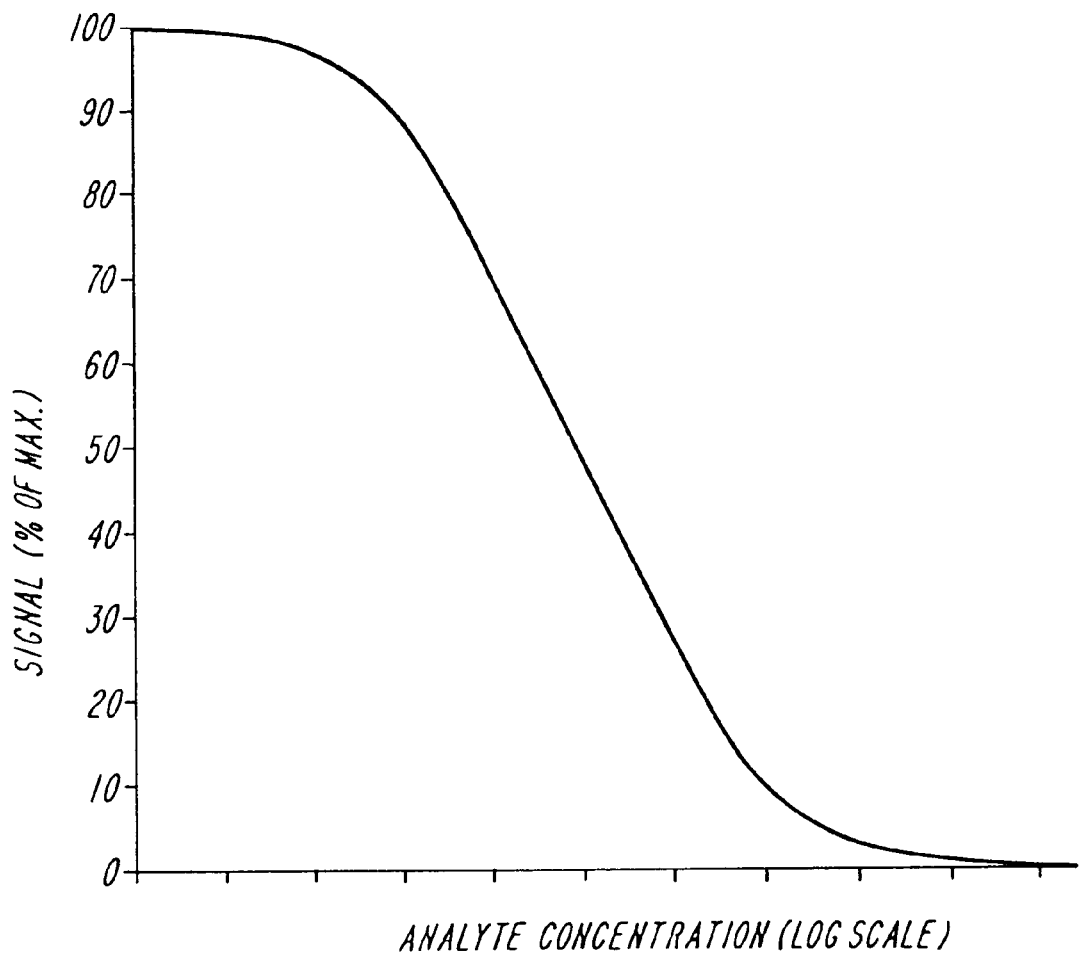
FIG. 1 is a generalized dose-response curve in standard competitive ligand-receptor assays.

The present competitive ligand-receptor device and method provides a competitive assay that eliminates the need for external calibration to obtain an accurate result. Thus, the present invention has a detection means that participates in two assays, with the signal intensities of both assays being related to the concentration of the analyte to be determined. The signal intensity of one of the assays is inversely related to the concentration of the analyte, and the signal intensity of the second assay is directly related to the concentration of analyte. The present assay thus can double the sensitivity in the maximum sensitivity range of a standard ligand-receptor competitive assay. Furthermore, the internal calibration feature allows a very precise determination of a threshold value of analyte for use in semiquantitative types of ligand-receptor assays. Finally, as will be discussed below, the internal calibration feature enables one skilled in the art to easily adjust the range of maximum sensitivity to match the predicted concentration range of analyte in a sample.

Thus, the present invention is directed to a device for the detection of at least one analyte in a sample solution, comprising a solid support containing a sample application zone, a particle zone, and one or more signal ratio areas. The sample application zone can be same or different from the particle zone. The particle zone contains one or more populations of particles capable of being transported along the solid support through the one or more signal ratio areas by the sample solution suspected of containing an analyte. Each population of particles is comprised of at least one sub-population of particles containing the first member of an inverse ligand-receptor pair, the first member of a direct ligand-receptor pair, and a signal means. Each signal ratio area is comprised of a first and second signal zone. For each population of particles, the first (inverse) signal zone contains the second member of an inverse ligand-receptor pair non-diffusively bound to the solid support. The second (direct) signal zone contains the second member of the direct ligand-receptor pair non-diffusively bound to the solid support. Furthermore, the number of signal ratio areas, the number of populations of particles, and the number of analytes are the same. It should be noted that in the present device, the sample application zone, the particle zone, and the one or more signal ratio areas are arranged in fluid communication such that a sample solution flows sequentially through the sample application zone, the particle zone, and then through the first and subsequently the second signal zone of each signal ratio area. The analyte to be detected is a member of an inverse ligand-receptor pair or an analog of such a member. The members of each inverse ligand-receptor pair neither cross-react with the members of any other inverse ligand-receptor pair nor cross-reacts with the members of any direct ligand-receptor pair, and vice-versa. Furthermore, the members of each inverse ligand-receptor pair do not cross-react with any non-analyte component of the sample solution. In any one population of particles, the total amount of the first member of an inverse ligand-receptor pair is less than the total amount of the second member of the same inverse ligand-receptor pair in the inverse signal zone; and the total amount of the first member of a direct ligand receptor pair is less than the total amount of the second member of the same ligand-receptor pair in the direct signal zone. Finally, each population of particles has a total amount of the first member of the inverse ligand-receptor pair such that one or more predetermined concentrations of analyte can be discerned in a signal ratio area from the ratio of signals in the first and second signal zones.

Figure 2:
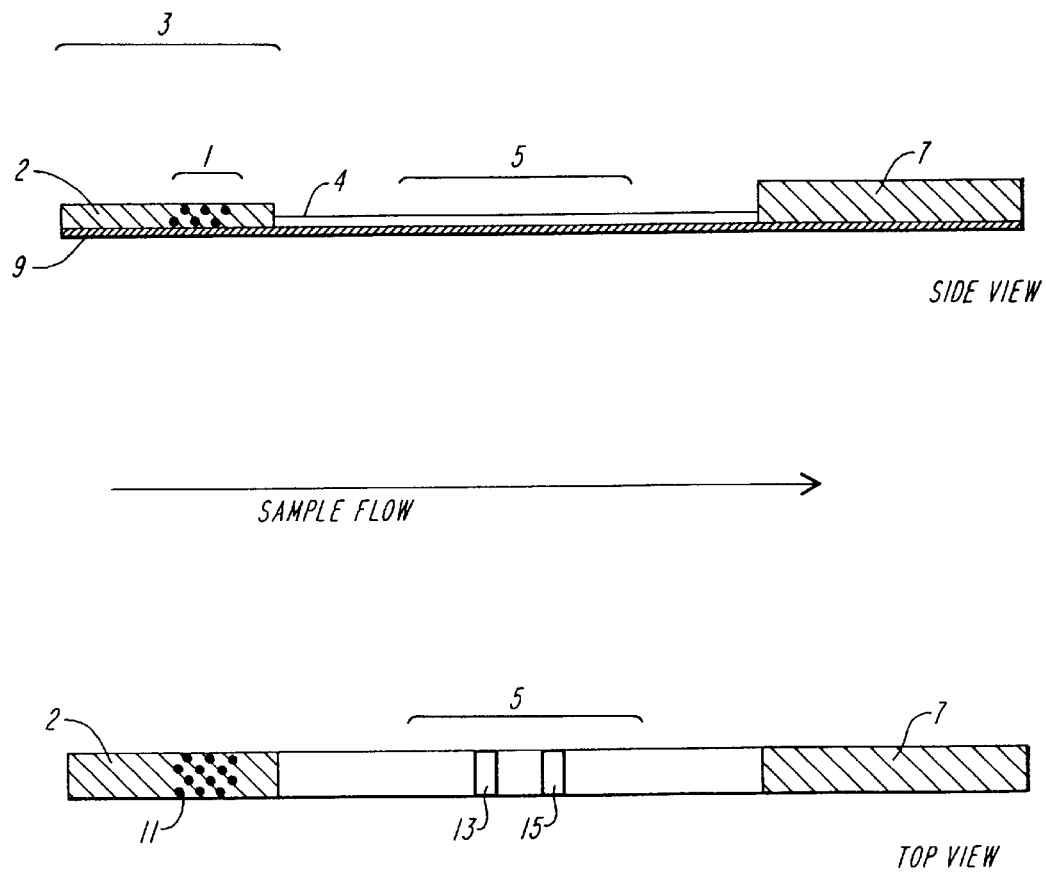
FIG. 2 is a schematic representation of one embodiment of the present invention, setting forth the particle zone (1), optional absorbent pad (2), sample application zone (3), wicking material (4), signal ratio areas (5), optional absorbent reservoir (7), optional backing material (9), particles (11), inverse signal zone (13) and direct signal zone (15).
Figure 3:
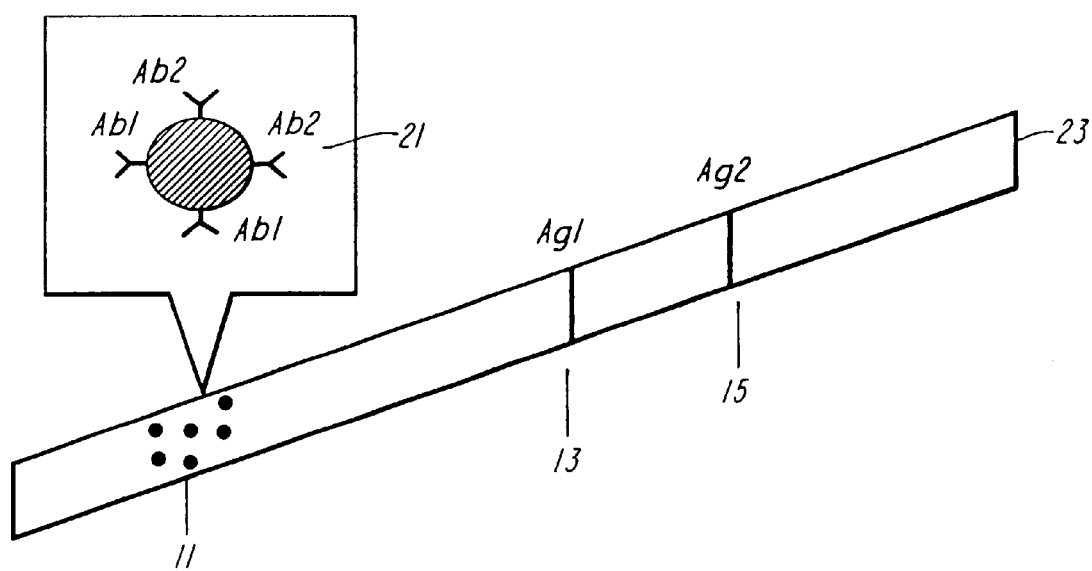
FIG. 3 demonstrates one embodiment of the present invention on an immunochromatographic test strip. An enlarged particle (21) from the particle zone (1) is shown above the solid support (23) and contains a first antibody (Ab1), referred to herein as the first member of the inverse ligand-receptor pair, which binds the analyte or an analog of the analyte either in the sample or in the inverse signal zone (13), and a second antibody (Ab2), referred to herein as the first member of the direct ligand-receptor pair, which binds to the antigen in the direct signal zone (15) on the test strip. The inverse signal zone (13) contains first antigen (Ag1), referred to herein as the second member of the inverse ligand-receptor pair, which is an analog of the analyte. The direct signal zone (15), contains a second antigen (Ag2), referred to herein as the second member of the direct ligand-receptor pair.

An example of such a device is represented schematically in FIG. 2. In the side view of this Figure, the particle zone (1) is part of a larger sample application zone (3) contained in an optional application pad (2). These two zones are in fluid communication with the one or more signal ratio areas (5) contained on wicking material (4), which in turn are in fluid communication with an optional absorbent reservoir (7). The particle zone (1), optional application pad (2), sample application zone (3), wicking material (4), the signal ratio area(s) (5) and the optional absorbent reservoir (7) comprises the solid support (23, FIGS. 3, 4, and 5), referred to above. In FIG. 2, all members of the solid support are shown mounted in the optional backing material (9). In the top view of FIG. 2, the particles (11) containing the first members and the signal means, are shown in the particle zone (1) as they exist before application of the sample. That is, they are shown as diffusively bound in an absorbent, non-particle-binding pad (2). One signal ratio area (5) is depicted, showing both the inverse signal zone (13) and the direct signal zone (15), wherein the second members are non-diffusively bound. The sample is applied to the sample application zone (3) and is wicked through the signal ratio areas (5), carrying with it the particles (11). Any excess sample that is not absorbed by the rest of the solid support along the way is eventually absorbed by the optional absorbent reservoir (7).

In the above device, the term "sample solution" means a fluid obtained from any organism or a solid sample obtained from such an organism and the relevant portion extracted or dissolved into a solution. For example, a sample can be a spinal fluid, urine, blood, serum, mucus, pus, tumor ascites, and material extracted from throat swabs, feces, or from other solid biological samples, as well as liquids or extracts from manufacturing lots in the pharmaceutical, food or cosmetic industry, effluents from industrial processes, or any other liquid suspected of containing an analyte.

The ligand-receptor pair will be compounds having spatial and/or polar features which permit it to bind specifically to each other. Ligand-receptor pairs useful in the present invention include specific binding pairs such as antigens and antibodies, or fragments of antibodies, both polyclonal and monoclonal, lectins and carbohydrates, hormones and hormone receptors, enzymes and enzyme substrates, biotin and avidin, vitamins and vitamin binding proteins, complementary polynucleotide sequences, drugs and receptors, enzymes and inhibitors, apoproteins and cofactors, growth factors and receptors, and the like. Biotin and avidin derivatives may also be used, including biotin analogs/avidin, biotin/streptavidin, and biotin analogs/streptavidin. Members of ligand-receptor pairs may be "engineered", that is, made by synthetic means. Such techniques are well known in the art, and include techniques for chimeric and humanized antibodies and fragments thereof, synthetic peptides, and synthetic RNA and DNA oligo-nucleotides. By "first member" of ligand-receptor pair is meant the member bound, covalently or non-covalently, at least to a sub-population of the particles. The "second member" of a ligand-receptor pair refers to the corresponding binding member of the pair non-diffusively bound in a signal ratio area.

By the term "inverse ligand-receptor pair" is meant the pair of which an analyte, or an analog of the analyte, is a member. This pair is so named because the signal intensity generated by this pair is inversely proportional to the concentration of analyte in the sample. Conversely, the "direct ligand-receptor pair" refers to the pair that does not contain the analyte or analyte analog. Thus, due to the spatial relationships of the two signal zones, signal intensity of the direct ligand-receptor pair will increase as the concentration of the analyte increases. Thus, the signal intensity of the direct ligand-receptor pair is directly proportional to the analyte concentration.

The particles in the particle zone can be a wide range of materials known in the art. At least one sub-population of these particles is composed of a first member of a ligand-receptor pair and a signal means, as discussed below. Thus, such particles can include enzymes such as glucose oxidase, horseradish peroxidase, alkaline phosphatase, galactosidase, or oxidoreductase. Such an enzyme, along with its signal producing system, such as described in Pawlak et al., International Patent Application No. WO 95/01775 published Jan. 20, 1994, herein incorporated by reference; a carbon sol (as discussed in Kang et al., U.S. Pat. No. 5,559,041, issued Sep. 24, 1996, herein incorporated by reference); erythrocyte ghosts, liposomes, and colored latex particles, (see Campbell et al., U.S. Pat. No. 4,703,017, issued Oct. 27, 1987, and Tarcha et al., U.S. Pat. No. 5,252,459, issued Oct. 12, 1993, both of which are herein incorporated by reference), colloidal metal particles, such as colloidal gold, colloidal silver, colloidal platinum and colloidal selenium (see, for example, Leuvering et al., U.S. Pat. No. 4,313,734, issued Feb. 2, 1982; Moremans et al., U.S. Pat. No. 4,775,636, issued Oct. 4, 1988; Yost et al., U.S. Pat. No. 4,954,452, issued Sep. 4, 1990, all of which are herein incorporated by reference). Colorable particles and colorable latex particles are also known in the art and useful as particles herein (see, for example, Gribnau et al., U.S. Pat. No. 4,373,932, issued Feb. 15, 1983, and de Jaeger et al., U.S. Pat. No. 4,837,168, issued Jun. 6, 1989, respectively, both of which are incorporated herein by reference.)

The first members of the ligand-receptor pairs may be covalently or non-covalently bound to the particles. This binding is accomplished by any method known in the art such as, for example, the use of glutaraldehyde and aminosilanes, as well as other methods described in "Immobilized Enzymes", Ichiro Chibata, Halstead Press, NY (1978); Cutrecasas, *J. Bio. Chem.*, 245:3059 (1970); March et al., *Anal. Biochem*, 60:149, et seq. (1974); Cantarero et al., "The Absorption Characteristics of Proteins for Polystyrene and Their Significance in Solid phase Immunoas says," *Analytical Biochemistry*, 105:375–382 (1980); and Bangs, "Latex Immunoassays," *J. Clin. Immunoassay*, 13:127–131 (1980), Weng et al., U.S. Pat. No. 4,740,468, issued Apr. 26, 1988 (see especially columns 13 through 15); Brown III et al., U.S. Pat. No. 4,916,056, issued Apr. 10, 1990; and U.S. Pat. Nos. 3,857,931; 4,181,636; and 4,264,766, all of which are incorporated herein by reference. The non-covalent binding takes advantage of the natural adhesion of first members to the non-synthetic and especially the synthetic fibers. Thus, appropriately buffered solutions can be mixed with the particles then evaporated, leaving a coating of the desired first member of the ligand-receptor pair on the particle.

The particles may be applied to the particle zone of the solid support by means known in the art. Various "printing" techniques have previously been proposed for application of such liquid reagents to carriers, for example, micro-syringes, pens using metered pumps, direct printing and ink-jet printing, and any of these techniques can be used in the present context. To facilitate manufacture, the solid support can be treated with the particles and then subdivided into smaller portions (e.g., small, narrow strips each embodying the required areas and zones) to provide a plurality of identical solid supports.

By the term "signal means" is meant any of the conventional methods known in the art detectable by methods such as visible inspection, UV and visible spectrophotometry, fluorimetry and radiation counters. In one embodiment, the signal means can be a property of the particles themselves. For example, the particles may themselves intrinsically be such a means when they are composed of a metal sol, a selenium sol or a carbon sol (see Leuvering et al., U.S. Pat. No. 4,313,734, issued Feb. 2, 1982; Moremans et al., U.S. Pat. No. 4,775,636, issued Oct. 4, 1988; Yost et al., U.S. Pat. No. 4,954,452, issued Sep. 4, 1990, and Kang et al., U.S. Pat. No. 5,559,041, issued Sept. 24, 1996, all of which have been incorporated by reference above), are colored latex particles (Campbell, U.S. Pat. No. 4,703,017, issued Oct. 27, 1987, incorporated by reference above) or is an enzyme that has reacted with a colorless substrate to give a colored product and is encapsulated, for example, in a liposome. (Pawlak et al., International Patent Application No. WO 94/01774, published Jan. 20, 1994, herein incorporated by reference). Alternatively, the signal means may be an inducible property of the particles, such as colorable latex particles (Gribnau et al., U.S. Pat. No. 4,373,932, issued Feb. 15, 1983, and de Jaeger et al., U.S. Pat. No. 4,837,168, issued Jun. 6, 1989, both incorporated by reference above).

Alternatively the signal means can be attached, either covalently or non-covalently, to either the particle itself, to one or more members of the ligand-receptor pair bound to the particle, or both. Such signal means can be a radioisotope, such as tritium, carbon 14, phosphorous 32, iodine 125, iodine 131, and the like. Fluorescent molecules, such as the rhodamine, fluorescein, or umbelliferone series, employed by themselves or with a quencher molecule, may be used. (See, for example, Ullman et al., U.S. Pat. No. 3,996,345, issued Dec. 7, 1976, and Tom et al., U.S. Pat. No. 4,366,241, issued Dec. 28, 1982, both of which are herein incorporated by reference.) Chemiluminescent molecules, such as luminol, luciferin, lucigenin, or oxalyl chloride can be used as a signal means (see, for example, Maier, U.S. Pat. No. 4,104,029, issued Aug. 1, 1978, herein incorporated by reference). Finally, enzymic systems that react with a colorless substrate to give a colored product, such as horseradish peroxidase and aminoethylcarbazole are useful as signal means.

Signal means that are detectable by visible inspection are preferred. Of these visible means, colored microparticles are optimum.

The present first members can be covalently bound to radioisotopes such as tritium, carbon 14, phosphorous 32, iodine 125 and iodine 131 by methods well known in the art. For example, $^{125}$I can be introduced by procedures such as the chloramine-T procedure, enzymatically by lactoperoxidase procedure or by the prelabelled Bolton-Hunter technique. These techniques plus others are discussed in H. Van Vunakis and J. J. Langone, Editors, *Methods in Enzymology*, Vol. 70, Part A (1980). See also, U.S. Pat. No. 3,646,346, issued Feb. 29, 1972, and Edwards et al., U.S. Pat. No.

4,062,733, issued Dec. 13, 1977, respectively, both of which are herein incorporated by reference, for further examples of radioactive labels. Similarly, the method of conjugation and use for fluorescent molecules can be found in the art. See, for example, J. J. Langone, H. Van Vunkais et al., *Methods in Enzymology*, Vol. 74, Part C (1981), especially at page 3 through 105. For a representative listing of other suitable fluorescent signaling means, see Tom et al., U.S. Pat. No. 4,366,241, issued Dec. 28, 1982, especially at column 28 and 29. For further examples, see also U.S. Pat. No. 3,996,345, herein incorporated by reference.

Further chemiluminescent signals, and means for binding them to the present particles and members, can be found in C. L. Maier, U.S. Pat. No. 4,104,029, issued Aug. 1, 1978, herein incorporated by reference.

Enzymatic signaling means include known in the art and include single an dual ("channeled") enzymes such as alkaline phosphatase, horseradish peroxidase, luciferase, β-galactosidase, glucose oxidase, lysozyme, malate dehydrogenase, glucose-6-phosphate dehydrogenase, and the like. Examples of dual ("channeled") catalytic systems include alkaline phosphatase and glucose oxidase using glucose-6-phosphate as the initial substrate. A second example of such a dual enzyme system is illustrated by the oxidation of glucose to hydrogen peroxide by glucose oxidase, which hydrogen peroxide would react with a leuco dye to produce a signal generator. (A further discussion of catalytic systems can be found in Tom et al., U.S. Pat. No. 4,366,241, issued Dec. 28, 1982, herein incorporated by reference. (See especially columns 27 through 40.) Also, see Weng et al., U.S. Pat. No. 4,740,468, issued Apr. 26, 1988, herein incorporated by reference, especially at columns 2 and columns 6, 7, and 8; and Litman et al., U.S. Pat. No. 4,843,000, issued Jun. 27, 1989, and Litman et al., U.S. Pat. No. 4,849,338, issued July 18, 1989, also incorporated herein by reference.)

The substrates for the catalytic systems include simple chromogens and fluorogens such as para-nitrophenyl phosphate (PNPP), β-D-glucose (plus optionally a suitable redox dye), homovanillic acid, o-dianisidine, bromocresol purple powder, 4-alkyl-umbelliferone, luminol, para-dimethylaminolophine, parametholxylophine, AMPPD, and the like. Preferred substrates for the enzymatic signal means are those that produce insoluble products. Examples of such preferred enzymatic signal means include aminoethylcarbazole and horseradish peroxidase; and bromochloroindolyl phosphate and nitro blue tetrazolium in conjunction with alkaline phosphate.

The procedures for coupling enzymes to the present first members are well known in the art and are described, for example, in J. H. Kennedy et al., *Clin. Chim Acta*, 70:1 (1976)). Reagents used for this procedure include glutaraldehyde, p-toluene diisocyanate, various carbodiimide reagents, p-benzoquinone m-periodate, $N,N_1$-o-phenylenedimaleimide, and the like.

The solid support referred to in the present invention has at least two, and preferably three, zones in fluid communication with one another. Thus, as stated above, there is a sample application zone panel which can be the same as the particle zone, and a least one signal ratio zone, all of which are in fluid communication with each other. It is preferred that the sample application zone and the particle zone be separate zones on a solid support. These zones and the one or more signal ratio areas are arranged as discussed above, and are all spatially distinct. The three zones can be arranged as a strip as set forth in FIGS. 2 through 5. The zones and the areas can all be on one piece of solid support, or one or more pieces support containing one or more zones, zone and areas, or areas can be abutted together on a suitable backing, or otherwise be made in fluid communication with each other on said backing. Thus, individual pieces of the zones can adhere to a backing by double-sided scotch tape. The backing can be, for example, plastic ribbon. See, for example, Rosenstein, U.S. Pat. No. 5,591,645, issued Jan. 7, 1997; Friesen et al., U.S. Pat. No. 4,861,711, issued Aug. 29, 1989; and May et al., European Patent Publication No. 291 194 B1, granted Feb. 16, 1994, all of which are herein incorporated by reference. The shape of the solid support can be that of longitudinal strips, a series of parallel strips, or that of a circular configuration, wherein the circular configuration can optionally be divided into various sections. For the latter configuration, see Kelton et al., U.S. Pat. No. 5,141,875, issued Aug. 25, 1992, herein incorporated by reference. All that is required is that the zones and areas are arranged as discussed above, and that the sample is able to traverse them in the order discussed. Thus, for the detection of more than one analyte, a strip with a sample application zone, a particulate zone, and more than one signal ratio areas are arranged sequentially along the length of the strip. Alternatively, for each analyte, a separate series of particulate zones and signal ratio areas can be placed in parallel on one comparatively wide strip. For a circular confirmation, the sample receiving zone would be placed at the center of the circle. Concentric rings radiating from the center, would first be the particle zone and then the one or more signal ratio zones. Alternatively, a common sample application zone could be used to supply the sample solution to two or more partitioned areas of the circular device containing separate particulate zones and one or more signal ratio areas.

The solid support may be porous material having pores of at least $0.1\mu$, preferably at least $1.0\mu$, which is susceptible to traversal by an aqueous medium in response to capillary force. Such materials are generally hydrophilic or are capable of being rendered hydrophilic and include inorganic powders such as silica, magnesium sulfate, and alumina; natural polymeric materials such as cotton, particularly cellulosic materials and materials derived from cellulose, such as fiber containing papers, e.g., filter paper, chromatographic paper, etc.; synthetic or modified naturally occurring polymers, such a nitrocellulose, cellulose acetate, fiberglass, poly(vinyl chloride), polyacrylamide, cross-linked dextran, agarose, polyacrylate, etc.; either used by themselves or in conjunction with other materials; ceramic materials; and the like. The solid support should not interfere with the signal means. This porous material can be attached to rigid or semi-rigid backing. On the other hand, the porous material may provide its own support. The porous material may be polyfunctional or be capable of being polyfunctionalized to permit covalent bonding of members of a ligand-receptor pair, as well as to permit bonding of any other components that are part of the device.

Further examples of the porous solid support of the present invention may be found in assays described, for example, in Friesen et al., U.S. Pat. No. 4,861,711, issued Aug. 29, 1989; Rosenstein et al., U.S. Pat. No. 5,591,645, issued Jan. 7, 1997; May et al., European Patent Publication No. 291,194, published Nov. 17, 1988; and Devereaux et al., EPO Publication No. 323,605, published Jul. 12, 1989, all of which are incorporated herein by reference.

Alternatively, the solid support of the present invention is fashioned from non-bibulous lateral flow material. By "non-bibulous" lateral flow is meant liquid flow in which all of the dissolved or dispersed components of the liquid are carried at substantially equal rates and with relatively unimpaired flow laterally through the membrane, as opposed to preferential retention of one or more components as would occur, for example, in materials capable of adsorbing or "imbibing" one or more components. "Bibulous" materials include paper, nitrocellulose, nylon and the like, which have the capability to effect a chromatographic separation of the contained materials.

An example of the non-bibulous solid support material in which capillary, non-bibulous lateral flow occurs is the high density or ultra high molecular weight polyethylene sheet material manufactured by Porex Technologies Corp. of Fairburn, Ga., USA. This solid support has an open pore structure with a typical density, at 40% void volume, of 0.57 g/cm$^2$ and an average pore diameter of 1 to 250 micrometers, the average generally being from 3 to 50 $\mu$m. While solid supports made of polyethylene have been found to be highly satisfactory, lateral flow, non-bibulous solid supports formed of other olefin or other thermoplastic materials, e.g., polyvinyl chloride, polyvinyl acetate, copolymers of vinyl acetate and vinyl chloride, polyamide, polycarbonate, polystyrene, etc., can be used. Membranes formed by the classical phase inversion process may also be used. Thus, the non-bibulous solid supports, in general, will have a pore size of about 3–100 $\mu$m, preferably about 10–50 $\mu$m; will be constructed of an inert material; and will optimally be less than 5 $\mu$m (200 mils) in thickness.

Bibulous materials, however, can be converted to those which exhibit nonbibulous flow characteristics by the application of blocking agents, in particular certain detergents and proteins, which obscure the interactive forces that account for the bibulous nature of the supports per se. Thus, nonbibulous solid support materials can be comprised of bibulous materials which have been blocked. Preferred blocking agents include bovine serum albumin, either per se or in methylated or succinylated form, whole animal sera, such as horse serum or fetal calf serum, and other blood proteins. Other protein blocking agents include casein and non-fat dry milk.

Detergent-based blocking agents can also be used. The types of detergents which are appropriate are selected from nonionic, cationic, anionic and amphoteric forms, and the selection is based on the nature of the membrane being blocked. Considerations which govern the selection of the appropriate detergent blocking agent are well understood in the art. It is preferred to use detergents in combination with protein-based blocking agents. Suitable detergents which can be used either alone or in admixture with the protein blocking agents include polyoxyethylene sorbitan alcohol detergents (i.e., the Tween series), polyoxyethylene alcohols such as Nonidet P-40 or polyoxyethylene ethers such as Triton X-100. The selection of blocking agent and formulation of the blocking composition is important, as the blocking must be sufficient to effect nonbibulous flow, but the modified surface must not interfere with ligand-receptor binding. Other embodiments of non-bibulous solid support are known in the art and can be found, for example, in Pawlak et al., International Patent Application WO 92/12428, and Sargent et al., European Patent Publication No. 296 724 B1, herein incorporated by reference.

Alternatively, the sample application zone and the particle zone would be combined and located on material different from the rest of the solid support. Such optional material, hereafter referred to as an application pad, would facilitate the mixing of the particles with the sample solution before the solution migrates through the one or more signal ratio areas. Thus, the application pad is also in fluid flow contact with the signal ratio areas. Fluid flow contact can include physical contact of the application pad to the rest of the solid support, as well as the separation of the pad from the solid support by an intervening space or additional material which still allows fluid flow between the pad and the support. Substantially all of the application pad can overlap the solid support to enable the test sample to pass through substantially any part of the application pad to the proximal end of the solid support. Alternatively, only a portion of the application pad might be in fluid flow contact with the solid support. The application pad can be any material which can transfer the test sample to the solid support and which can absorb a volume of sample that is equal to or greater than the total volume capacity of the remaining solid support.

Materials preferred for use in the optional application pad include nitrocellulose, porous polyethylene filter pads and glass fiber filter paper. The material must also be chosen for its compatibility with the analyte and assay reagents.

In addition, the optional application pad can contain one or more assay reagents either diffusively or non-diffusively attached thereto. Reagents which can be contained in the application pad include buffers, preservatives, detergents, bacteriostats, ancillary ligand-receptor members, and any signal means components, such as enzyme substrates. For further discussion of such as application pad, see Devereaux et al., European Patent Publication No. 323 605 B1, granted Jan. 26, 1994, herein incorporated by reference.

The solid support can have a reasonable inherent strength, or strength can be provided by means of additional backing. The backing for the solid support where a support is desired or necessary can be water insoluble, non-porous, and rigid and usually will be of the same length and width as the solid support but can be larger or smaller. A wide variety of organic and inorganic materials, both natural and synthetic, and combinations thereof, can be employed provided only that the backing does not interfere with the capillary action of the strip, or non-specifically bind assay components, or interfere with the signal means. Illustrative materials include polyethylene, polypropylene, poly(4-methylbutene), polystyrene, polymethacrylate, poly(ethylene terephthalate), nylon, poly(vinyl butyrate), glass, ceramics, metals, and the like.

The solid support can be a single structure such as a sheet cut into strips or it can be particulate material bound to a support or solid surface such as found, for example, in thin-layer chromatography.

The particular dimensions of the solid support will be a matter of convenience, depending upon the size of the sample involved, the assay protocol, the means for detecting and measuring the signal, and the like. For example, the dimensions may be chosen to regulate the rate of fluid migration as well as the amount of sample to be imbibed by porous solid support.

Optionally, the solid support can be partially or fully enclosed in a moisture-impermeable, inert casing that can be transparent, translucent, or opaque, as known in the art. Such a casing would ideally have at least two apertures, one above the sample application zone and one above the signal ratio area. The aperture above the signal ratio area could be covered with a transparent material. Alternatively, no apertures above the sample receiving zone would be necessary if a bibulous means was provided to the exterior of the casing and to the solid support below the sample receiving zone such that the sample would be wicked in and applied to the solid support. Examples of such casings can be found in May et al., European Patent Publication No. 290 194 B1, granted Feb. 16, 1994.

By the term "non-diffusively bound" is meant the second members of the inverse and direct ligand-receptor pairs are either covalently or non-covalently attached to the solid support such that advancing solution liquid phase does not cause either member of the pair to move from the place it is applied on the solid support.

The second members of the ligand-receptor pairs may be non-diffusively bound by direct or indirect means directly to the solid support. The solid support may have been previously derivatized prior to the application of the second member. The direct binding can be covalent or non-covalent. Covalent binding can be accomplished by using a solid support derivatized with reactive groups such as amino, chloromethyl, aldehyde, carboxyl, epoxy, and the like. Covalent binding can also be accomplished by any method known in the art such as, for example, the use of glutaraldehyde, aminosilanes, cyanogen bromide, carbonyldiimidazole, ethyl chloroformate, 1-(3-nitrobenzyloxy-methyl)-pyridimium chloride (NBPC) and treslyl chloride, as well as other methods described in "Immobilized Enzymes", Ichiro Chibata, Halstead Press, NY (1978); Cutrecasas, *J. Bio. Chem.*, 245:3059 (1970); March et al., *Anal. Biochem.*, 60:149, et seq. (1974); and Tijssen et al., *Practice and Theory of Enzyme Immunoassays*, Chapter 3, Elsevier Science Publishers, (1985). The non-covalent binding takes advantage of the natural adhesion of second members to the non-synthetic and especially the synthetic fibers. Thus, appropriately buffered solutions can be mixed with the solid support then evaporated, leaving a coating of the desired second member of the ligand-receptor pair on the membrane.

The non-direct method for applying the second members to the solid support employs either covalently or non-covalently binding the second members to microparticles. Such microparticles may then be bound to or entrapped by the solid support such that the microparticles are within the matrix of the membrane, on the surface of the membrane, or bound to other microparticles which are in turn bound to the membrane. The size of the microparticles should be such that they do not migrate through the membrane to any significant degree. The microparticles may be made of a variety of naturally-occurring or synthetic materials, such as microparticles are those made from polyethylene, polystyrene, agarose, dextran, cellulose, starch, or the like and the aldehyde, carboxyl, amino, hydroxyl, or hydrazide derivatives thereof. The binding of the second member to the microparticle may be by methods similar to those discussed above for binding the second member directly to the solid support or other methods known to those skilled in the art, as discussed above for the preparation of the particles.

The second members, whether bound to a microparticle or not, can be applied to the solid support by the means discussed above for applying the microparticles containing the first members. In applying the second members to the solid support, it is necessary that the inverse signal zone(s) span the width and the depth of the solvent front created by any fluid traversing through the solid support. Such fluid may be the sample solution, a wicking fluid as described below, or a solution containing the substrate for an enzymatic signal means. It is optimal, but not necessary, that the direct signal zones be the same width as the inverse signal zones.

The analytes to be determined using the methods and devices of the present invention are defined primarily by their ability to be a part of a ligand-receptor pair. Generally, the molecular weight of an analyte will be between 100 and about 100,000; however, the present method can be applied to detect macro-molecules of a much higher molecular weight. Antigens, haptens and their antibodies, hormones, vitamins, drugs, metabolites and their receptors and binding materials, fungicides, herbicides, pesticides, plant, animal and microbial toxins, may be determined using the present method. Representatives of analytes determinable by the methods and devices of the present invention include steroids such as estrone, estradiol, cortisol, testosterone, progesterone, chenodeoxycholic acid, digoxin, cholic acid, digitoxin, deoxycholic acid, lithocholic acids and the ester and amide derivatives thereof; vitamins such as B-12, folic acid, thyroxine, triiodothyronine; histamine; serotonin; prostaglandins such as PGE, PGF, PGA; antiasthmatic drugs such as theophylline, antineoplastic drugs such as doxorubicin and methotrexate; antiarrhythmic drugs such as disopyramide, lidocaine, procainamide, propranolol, quinidine, N-acetylprocainamide; anticonvulsant drugs such as phenobarbital, phenytoin, primidone, valproic acid, carbamazepine and ethosuximide; antibiotics such as penicillins, cephalosporins, erythromycin, vancomycin, gentamicin, amikacin, chloramphenicol, streptomycin and tobramycin; antiarthritic drugs such as salicylate; antidepressant drugs including tricyclics such as nortriptyline, amitriptyline, imipramine and desipramine; and the like as well as the metabolites thereof.

Additional analytes that may be determined by the methods and device of the present invention include drugs of abuse such a morphine, heroin, hydromophone, oxymorphone, metapon, codeine, hydrocodone, dihydrocodiene, dihydrohydroxy codeinone, pholcodine, dextromethorphan, phenazocine, deonin and their metabolites. Higher molecular weight analytes such as amino acids, polypeptides, antibodies and proteins such as hCG, TSH, LH, FSH, ferritin, CEA, PSA, insulin, hemoglobin, growth hormone, C-reactive protein, as well as infectious disease agents (i.e., of bacterial or viral origin, such as Streptococcus, Neisseria, and Chlamydia) may also be determined by the methods and devices of the present invention.

An analog of such an analyte is simply a molecule that binds to other member of the ligand-receptor pair in approximately the same specificity as the analyte itself.

Antibodies, and fragments thereof, suitable for use in this invention are obtained by techniques known to the art. For instance, polyclonal antibodies are obtained by immunizing a species of animal that differs from the species producing the antigen (analyte of interest). Monoclonal antibodies are obtained by fusing the splenocytes of an immunized mouse with a plasmacytoma cell line by the addition of polyethylene glycol to the cell mixture, thereby forming hybridoma cells which are suspended and then plated to tissue culture plates. Only the cultures producing antibodies that are immunologically reactive with antigen are cloned. See for example, David et al., U.S. Pat. No. 4,376,110, issued Mar. 8, 1983, which teaches the preparation of monoclonal antibodies and is incorporated herein by reference.

Figure 6:
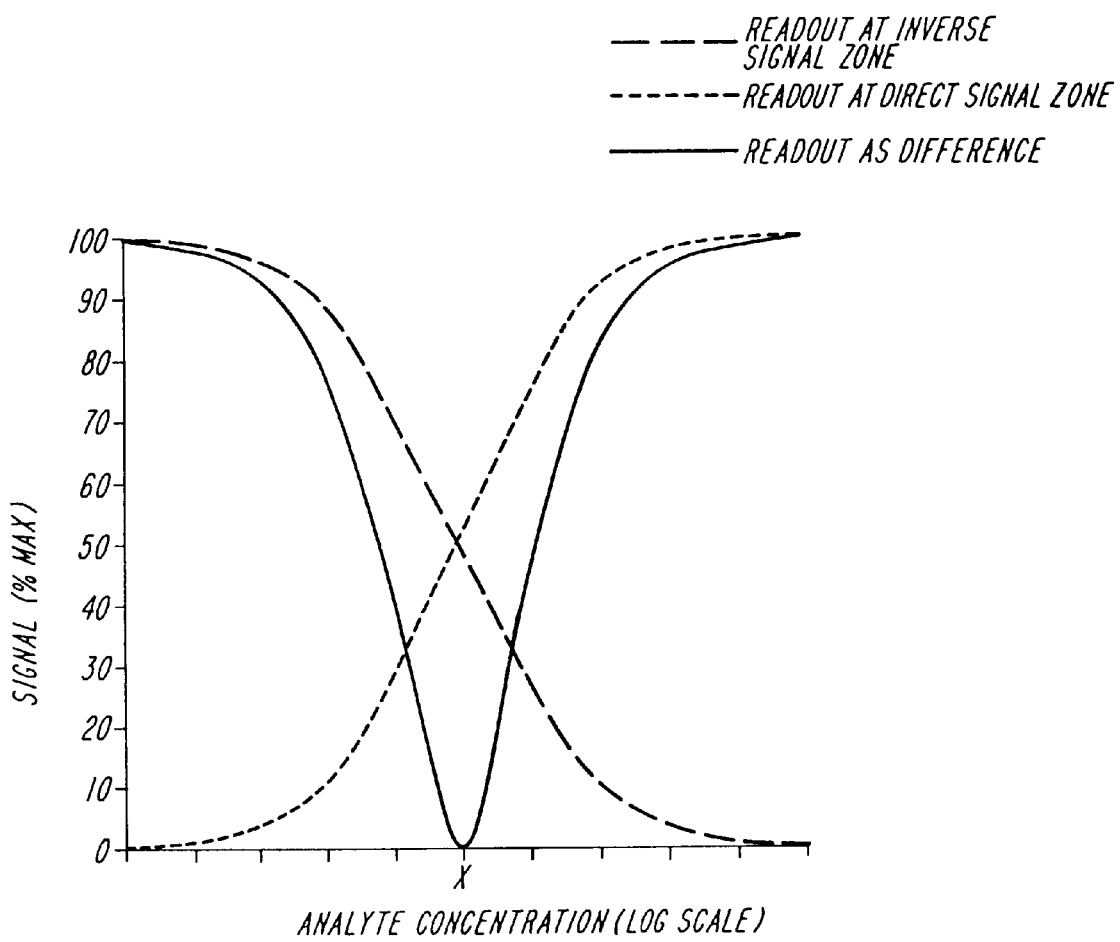
FIG. 6 demonstrates the dose response curve for the present internally calibrated competitive ligand-receptor assay.

The two signal zones in each signal ratio area are placed far enough from the particle zone to allow sufficient binding of the analyte to the first member of the inverse ligand-receptor pair on the particle before it reaches the signal ratio area. In the signal ratio area, the two signal zones are in spatial proximity as mentioned above and are close enough such that detection of each individual signal and comparison of the two signals is facilitated. It is imperative that the particles and the sample solution suspected of containing the analyte first go through the first signal zone before entering the second signal zone. Furthermore, it is necessary that the amount of each second member bound to the solid support is greater than the total amount of corresponding first member of a ligand-receptor pair in the population of particles for specific analyte. It is also imperative that no member of any ligand-receptor pair cross-react with any other member of a ligand-receptor pair, be it inverse or direct, or with any non-analyte component of the sample solution. As mentioned above, the ratio of the two signal zones can be determined by visual inspection, by spectrophotometric means, or by radiation counters, or by any other method known in the art. As the signal generated in the two signal zones is related to the concentration of one analyte, the comparison will give an accurate rendering of at least a threshold, pre-determined concentration of the analyte. The relationship between the two signals is illustrated in FIG. 6. Thus, the possibilities of signal intensity ratios between the two zones set forth in Table 1 can be imagined.

TABLE 1

| Entry No. | First Signal Zone | Second Signal Zone | Ratio/ $Signal_1/Signal_2$ |
|---|---|---|---|
| 1 | No Signal | Detectable Signal | $1/\infty$ |
| 2 | Equal Signal | Equal Signal | 1 |
| 3 | Some Detectable Signal | No Detectable Signal | $\infty$ |
| 4 | Detectable Signal, but Less Than Second Zone | Detectable Signal, More Than First Zone | <1 |
| 5 | Detectable Signal, More Than Second Zone | Detectable Signal, Less Than First Zone | >1 |

Figure 4:
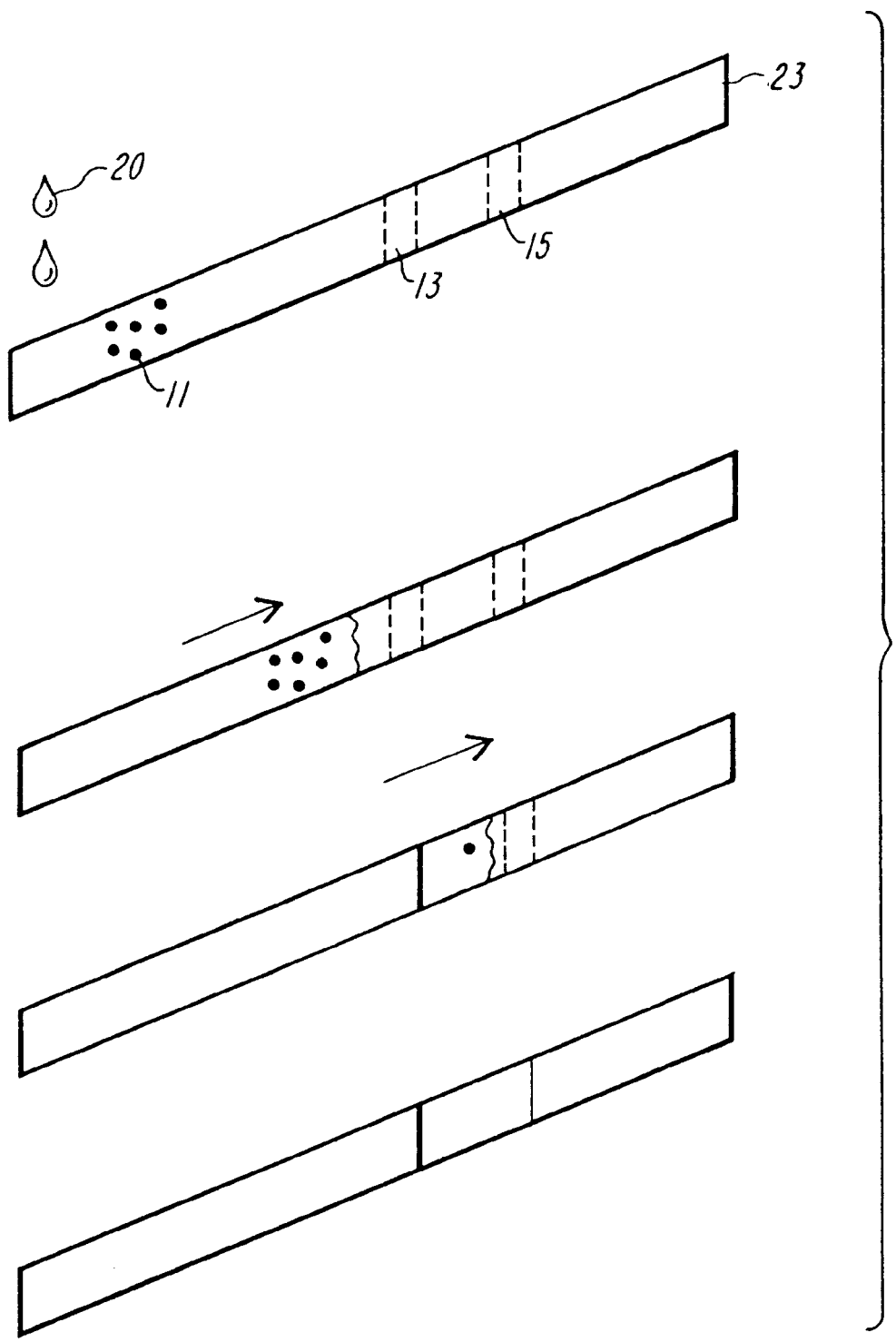
FIG. 4 demonstrates the possible outcome of an assay depicted in FIG. 3 where the sample (20) contains little or no analyte. Thus, the first, inverse signal zone (13) has a much higher intensity signal than the second, direct signal zone (15).
Figure 5:
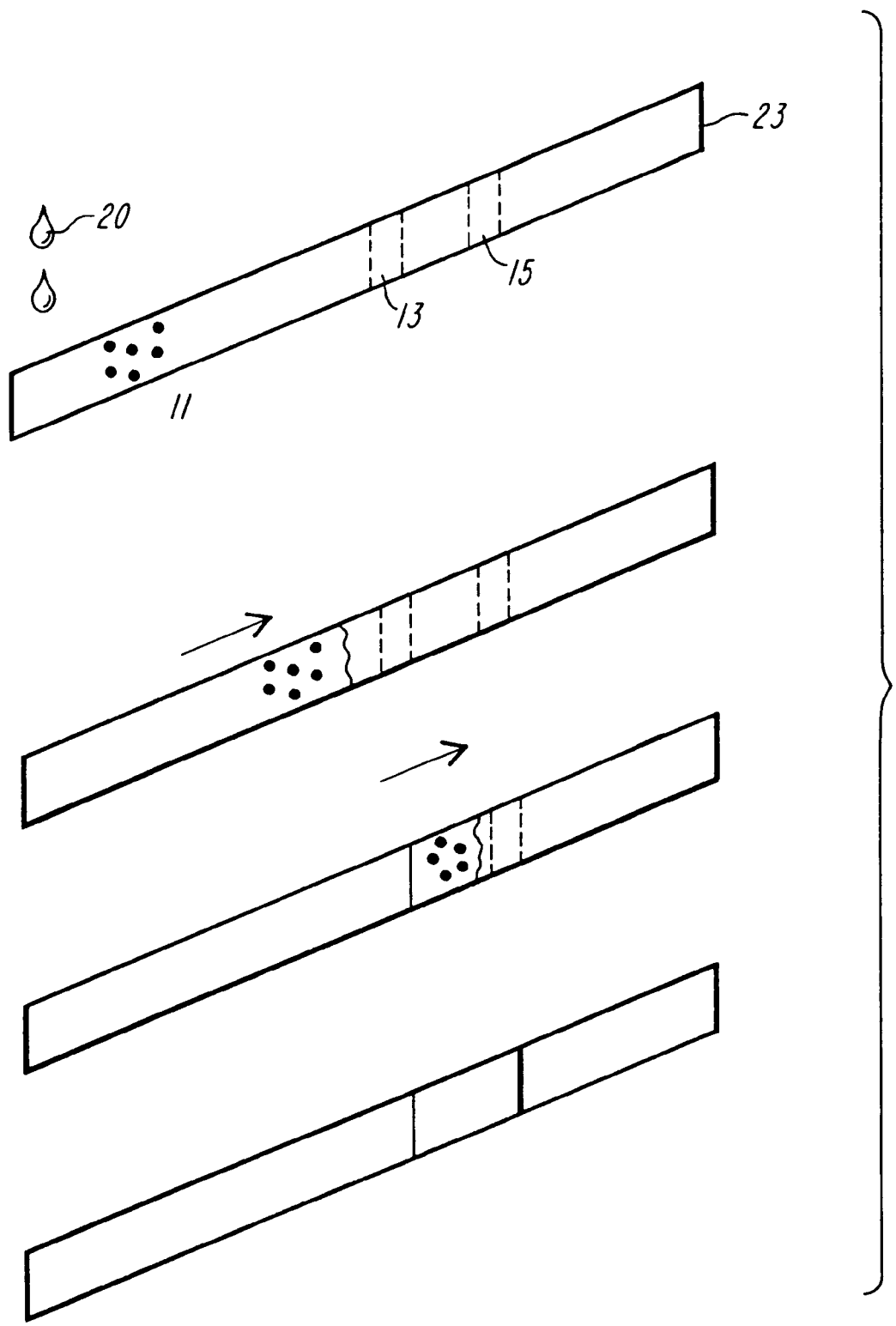
FIG. 5 demonstrates the opposite possibility of FIG. 4, wherein the sample (20) has a high concentration of analyte. Thus, the signal in the second, direct signal zone (15) is much higher than that in the first, inverse signal zone (13).

Entries 4 and 5 in the above Table 1 are represented in FIGS. 5 and 4, respectively.

Combinations of the above possible ratios can be used to predict more than one predetermined concentration of analyte in a sample. Thus, one can control the amount of the inverse ligand-receptor pair on the particle such that no signal in the first signal zone and some in the second signal zone is indicative of one concentration of analyte. An equal amount of signal in both zones is the second concentration and detectable signal in the first zone and no detectable signal in the second zone is the third concentration. Any one or more of the above possible outcomes can be imagined to give such a multiple analyte concentration reading.

Furthermore, the population of particles in the particle zone can be manipulated to shift the range of maximum sensitivity for any one given analyte. Thus, a subpopulation of particles containing only one of the two first members of either the inverse ligand-receptor pair or the direct ligand-receptor pair, in addition to the signaling means. By this method, the signal intensity in one or the other zone can be intensified independent of the concentration of the analyte.

The present method utilizes the device described above to detect one or more analytes in a quantitative, semi-quantitative, or qualitative fashion for analytes found in a sample solution. Specifically, the method entails applying a sample solution suspected of containing an analyte to a device at the signal application zone described above that as a signal ratio zone capable of detecting the analyte. The sample solution is applied in the sample application zone. The sample solution is allowed to flow sequentially through the particle zone in the one or more signal ratio areas. Then the signal ratio areas are inspected either visually, by radiophotographic film, spectrophotometrically, by densitometry, or by radiation counter, for example, to determine the ratio of the signals in the two zones. The determined ratio gives a quantitative, semi-quantitative or qualitative indication of the concentration of analyte present.

In the method, the sample can be applied to the sample application zone as a viscous sample or a solid sample. Optionally, a wicking fluid can be subsequently applied to sample application zone such that the analyte is dissolved or suspended in the wicking solution and the wicking solution traverses the particle zone and the one or more signal ratio zones in the proper fashion. When an aqueous test sample is used, a wicking solution generally is not necessary but can be used to improve flow characteristics or adjust the pH of the sample solution. In general, the wicking solution used in the present invention typically has a pH range from about 5.5 to about 10.5, and more preferably from about 6.5 to about 9.5. The pH is selected to maintain a significant level of binding affinity between the ligand-receptor pairs. When one member of a ligand-receptor pair is an enzyme, the pH also must be selected to maintain a significant level of binding affinity between the members of the pair. When the signal means is an enzyme, the pH also must be selected to maintain significant enzyme activity for color development in enzymatic signal production systems. Illustrative buffers include phosphate, carbonate, barbital, diethylamine, tris, 2-amino-2-methyl-1-propanol, and the like. The wicking solution and the sample can be combined prior to contacting the application pad or they can be contacted to the application zone sequentially.

In order to determine the ratio in the signal ratio areas, for certain of the signal means, it is necessary to supply separate signal generation substance, such as a substrate for an enzyme, before detecting the ratio. Thus, if the signal means is an enzyme that converts a colorless substrate to a colorful product, (e.g., horseradish peroxidase and aminoethylcarbazole) then the substrate is applied simultaneously with or after the application of the sample solution.

As a matter of convenience, the present device can be provided in a kit in packaged combination with predetermined amounts of reagents for use in assaying for an analyte. Where an enzyme is used as the label, the substrate for the enzyme or precursors therefor including any additional substrates, enzymes and cofactors and any reaction partner of the enzymic product required to provide the detectable signal can be included. In addition, other additives such as ancillary reagents can be included, for example, stabilizers, buffers, and the like. The relative amounts of the various reagents can be varied widely, to provide for concentrations in solution of the reagents which substantially optimize the sensitivity of the assay. The reagents can be provided as dry powders, usually lyophilized, including excipients, which on dissolution will provide for a reagent solution having the appropriate concentrations for performing the assay. The kit can also be contained in packaging material, such as air-tight foil, or various external containers known in the art. Such external containers can contain the device, reagents, and the instructions for use of the device.

The invention can be better understood by way of the following examples which are representative of the preferred embodiments thereof, but which are not to be construed as limiting the scope of the invention.

EXAMPLE I

Semi-Quantitative Determination of Penicillin

This procedure details the use of the invention in the semi-quantitative determination of penicillin in aqueous samples using an immunochromatographic test strip embodying the present invention. The assay informs the user whether the concentration of penicillin is above or below a pre-set value, in this example 100 ng/ml. The assay utilizes colored latex spherical particles as the label and monoclonal antibodies as ligand receptors. During the assay, color development occurs at two sites, with the color intensities being equal at the two sites at 100 ng/ml of penicillin in the sample; differences in color intensities at the two sites indicate whether the concentration of penicillin is above or below 100 ng/ml. For the purpose of demonstration, the assay was performed on spiked samples containing penicillin G sodium in phosphate-buffered saline at concentrations of 0, 10, 50, 100, 200, 500, and 1000 ng/ml.

1. Preparation of Colored Latex Particles.

Monoclonal antibody specific for penicillin which also wound bind penicillin-BSA (bovine serum albumin covalently bound to penicillin analog) ligand analog, and monoclonal antibody specific for ovalbumin were prepared according to standard procedure (Nelson et al., *Immunoanalysis of Agrochemicals*, American Chemical Society, Washington, D.C., 1995; Harlow and Lane, *Antibodies, a Laboratory Manual*, Cold Springs Harbor Laboratory, Cold Spring Harbor, N.Y., 1988). Binding of anti-penicillin antibodies to penicillin-BSA and binding of these anti-ovalbumin antibodies to ovalbumin was verified using an indirect enzyme-linked immunosorbent assay (ELISA), where antigens were passively adsorbed onto polystyrene microtiter plates and the binding of the monoclonal antibodies was detected by alkaline phosphatase-labeled goat anti-mouse IgG antibody (American Qualex, Fullerton, Calif.). Free penicillin G sodium was shown to compete with penicillin-BSA for binding to anti-penicillin antibody in the ELISA, but not the binding of anti-ovalbumin to ovalbumin.

Monoclonal antibodies were purified from ascites and used at a concentration of 0.2–0.4 mg/ml in 20 mM Tris buffer, pH 7.2. Polystyrene latex spherical particles dyed blue, with a mean diameter of 0.219 microns (Polysciences, Warrington, Pa.) containing 2.5% solids were used as received from the manufacturer. Anti-penicillin antibody (72 ug) was mixed with anti-ovalbumin antibody (172 ug) in a total volume of 1.5 ml of 20 mM Tris buffer, pH 7.2. To this solution was added a solution of the above latex particles (0.14 ml) and the resultant mixture was incubated at room temperature for 30 minutes. Based on the calculation of available surface area of the latex particles, the total amount of antibody added in this step was less than the binding capacity of the particles. This, it was expected that essentially all added antibody adsorbed to the particle surface. To block the remaining protein adsorption sites on the particles, a solution composed of 5% BSA, 6% sucrose, and 0.025% Bioterge surfactant (Pragmatics, Elkhart, IN) in 100 mM Tris buffer (1.0 ml), pH 8.4 was added and the suspension was stirred for 1 hour at room temperature. The resultant latex suspension remained stable for at least 24 hours.

2. Preparation of Test Strips.

The members of the two ligand-receptor pairs were applied across 30 cm-wide sheets of nitrocellulose sheet wicking material using a volumetric dispenser mounted onto a precision X-Y motion controller (Biodot, Irvine, Calif.). Inverse second member analog penicillin-BSA (4 mg/ml in 20 mM Tris buffer, pH 8,4) and direct second member ovalbumin (4 mg/ml in 20 mM Tris buffer, PH 8,4) were dispensed onto the nitrocellulose sheet (approximately 10 micron pore size, 2.5 cm×30 cm, Millipore, Fairburn, Ga.) so that a 1 mm wide line of each reagent was applied across the 30 cm width of the nitrocellulose sheet. The penicillin-BSA line was applied 1.3 cm from one edge of the nitrocellulose, and the ovalbumin line 1.9 cm from the same edge. The nitrocellulose sheet was then allowed to air dry at room temperature. Using the same dispensing method, the latex microsphere suspension from Step 1 above was dispensed onto sheets of glass fiber (Millipore, Bedford, Mass.) (2 cm ×30 cm). The optional glass fiber sheets were first blocked by applying 30 ul per centimeter of width of a solution composed of 15% BSA, 6% sucrose, 0.25% Biterge surfactant in 100 mM Tris buffer, pH 8.4, and then drying the sheets at room temperature or at 45° C. The latex suspension was applied onto the blocked glass fiber at a rate of 12.5 ul per centimeter of width, so that a blue stripe, approximately 0.5 cm wide, appeared 3 mm from one edge of the glass fiber sheet. The glass fiber sheets were then dried as above and stored in a desiccation until final assembly.

In the final assembly, test strip materials were laminated in the orientation shown in FIGS. 2 through 5. First, nitrocellulose wicking material was laminated onto adhesive plastic backing (6 cm×30 cm, 10 mil thick) at a distance of 1.7 cm from one edge of the backing and 2.8 cm from the other edge, with the ovalbumin reagent line being nearest the 2.8 cm width. The optional sample application pad composed of the glass fiber treated as above was laminated onto the 1.7 cm side of the backing, so the one edge of the glass fiber overlaid the nitrocellulose wicking material by approximately 0.25 cm. The optional absorbent pad (cellulose absorbent pad, 2.5 cm×30 cm×1 mm thick, Gelman Sciences, Pensacola, Fla.) was laminated onto the 2.8 cm side of the backing, so that one edge overlaid the nitrocellulose wicking material by approximately 0.25 cm. The assembly, 30 cm wide, was cut into 0.5 cm wide units, which units were the test strips used below. These test strips are illustrated in FIG. 2.

3. Performing the Assay.

Spiked penicillin samples were prepared by dissolving penicillin G sodium (Sigma Chemical, St. Louis, Mo.) in phosphate-buffered saline to achieve final antibiotic concentrations of 0, 10, 50, 100, 200, 500, and 1000 ng/ml. Each of these samples was run on three separate test strips. In each assay, a portion of the sample (100 $\mu$l) was placed at the bottom of a small test tube (12×75 mm, Fisher), and a test strip was then placed in the test tube so that the sample application zone was in contact with the sample. The sample then moved through the porous elements of the strip by capillary action. The fluid flow redissolved the dried latex particles and moved them through the optional sample application pad and the nitrocellulose wicking material, depositing blue lines at the site of the penicillin-BSA reagent (Inverse signal zone, Line 1) and at the site of the ovalbumin reagent (Direct signal zone, Line 2). The flow of sample stopped when the optional absorbent pad was saturated (approximately 15 minutes), but color development at the two signal zones was finished before the flow stopped (less then 7 minutes).

Interpretation of results was performed visually by a person who was not aware of the identity of the samples. The person was asked whether "Line 1" (the inverse signal zone) was darker than "Line 2" (the direct signal zone) or vice versa. The results (Table 2) indicated the assay unequivocally identified the samples containing less than 100 ng/ml and the samples containing more than 100 ng/ml of antibiotics. Additionally, the threshold point was also identified with precision.

TABLE 2

RESULTS OF PENICILLIN ASSAY WITH THRESHOLD AT 100 NG/ML

| Penicillin Concentration (ng/ml) | No. of samples with Line 1 darker than Line 2 (Negative) | No. of samples with Line 1 about equal to Line 2 | No. of samples with Line 1 lighter than Line 2 (Positive) |
|---|---|---|---|
| 0 | 3/3 | 0/3 | 0/3 |
| 10 | 3/3 | 0/3 | 0/3 |
| 50 | 3/3 | 0/3 | 0/3 |
| 100 | 0/3 | 3/3 | 0/3 |
| 200 | 0/3 | 0/3 | 3/3 |
| 500 | 0/0 | 0/0 | 3/3 |
| 1000 | 0/3 | 0/3 | 3/3 |

EXAMPLE II

Semi-Quantitative Immunoassay for Penicillin with Different Threshold Concentrations This example details the modification of the assay in Example I to change the threshold concentration of analyte detected while using the same reagents. The procedure below describes a method of changing the amounts of ligand receptors (anti-penicillin antibody) in the assay in order to move the analyte concentration at which the color development at the inverse and direct signal zones are equal.

1. Preparation of Colored Latex Reagent.

Antibodies and other reagents were the same as used in Example I. To change the threshold concentration, the amount of anti-penicillin antibody was changed, while all other parameters were held constant, including the amount of anti-ovalbumin, the blocking reagents, volumes, and buffers. Anti-penicillin antibody was added to the anti-ovalbumin antibody in the amounts listed in Table 3, and thereafter the latex preparation proceeded exactly as in Example I.

2. Preparation of Test Strips.

Test strips were prepared identically to those in Example I.

3. Performing the Assay.

Spiked penicillin samples were prepared by dissolving penicillin G sodium (Sigma Chemical) in phosphate-buffered saline to give final antibiotic concentrations of 5, 10, 20, 30, 40, 50, 75, 100, 150, 200, 250, 300, 400, 500, and 1000 ng/ml. Assays were run in the same manner as in Example I. For each preparation of latex particles, the corresponding set of test strip assays was performed on the range of penicillin concentrations. An independent viewer then determined the concentration of penicillin at which the color intensities at Line 1 (inverse signal zone) and Line 2 (direct signal zone) were the most similar (results in Table 3). These results demonstrate the ease of moving the threshold concentration of analyte in a semi-quantitative assay within a 50-fold range.

TABLE 3

RESULTS OF EXAMPLE II

| Preparation of Latex Particles (11) | Amount of Anti-Penicillin Antibody (ug) | Penicillin Concentration at Threshold (ng/ml) |
|---|---|---|
| 1 | 20 | 20 |
| 2 | 32 | 40 |
| 3 | 45 | 75 |
| 4 | 72 | 100 |
| 5 | 78 | 150 |
| 6 | 85 | 200 |
| 7 | 150 | 1000 |

Although the invention has been described with reference to the examples provided above, it should be understood that various modifications can be made without departing from the spirit of the invention. Accordingly, the invention is limited only by the claims.

What is claimed is:

1. A device for the detection of at least one analyte in a sample solution, comprising a solid support containing:
    (a) a sample application zone, which can be the same or different from a particle zone;
    (b) the particle zone, which contains at least one population of particles which are transported along the solid support by the sample solution suspected of containing the analyte, wherein the population of particles is composed of at least one subpopulation of particles containing the first member of an inverse ligand-receptor pair, the first member of a direct ligand-receptor pair, and a signal means; and
    (c) at least one signal ratio area, comprising a first and a second signal zone wherein, for the population of particles, the first signal zone contains the second member of an inverse ligand-receptor pair non-diffusively bound to the solid support, and the second signal zone contains the second member of the direct ligand-receptor pair non-diffusively bound to the solid support;

wherein:
    the above elements are arranged in fluid communication whereby a sample solution suspected of containing an analyte flows sequentially through the sample application zone, the particle zone and then through the first and subsequently the second signal zone of each signal ratio area;
    the analyte is a member of an inverse ligand-receptor pair or an analog thereof;
    the members of each inverse ligand-receptor pair neither cross-react with the members of any other inverse ligand-receptor pair nor cross-react with the members of any direct ligand-receptor pair and vice-versa, nor with any non-analyte component of the sample solution;
    in any one population of particles, the total amount of the first member of an inverse ligand-receptor pair is less than the total amount of the second member of the same inverse ligand-receptor pair in the inverse signal zone; and the total amount of the first member of a direct ligand receptor pair is less than the total amount of the second member of the same ligand-receptor pair in the direct signal zone; and
    at least the one population of particles has a total amount of the first member of the inverse ligand-receptor pair whereby one or more predetermined concentrations of analyte can be discerned in a signal ratio area from a ratio of signals in the first and second signal zones.

2. A device of claim 1, wherein a population of particles in the particle zone further contains a sub-population of particles with only the first member of the inverse ligand-receptor pair and a signal means.

3. A device of claim 1, wherein a population of particles in the particle zone further contains a sub-population of particles with only one member of the direct ligand-receptor pair and a signal means.

4. A device of claim 1, wherein the signal means is a visible particle.

5. A device of claim 1, wherein the signal means is a colored latex particle.

6. A device of claim 1, wherein the inverse ligand-receptor pair is an antibody-antigen pair.

7. A device of claim 1, wherein the direct ligand-receptor pair is avidin and biotin.

8. A device of claim 1, wherein the solid support is in the form of a strip.

9. A device of claim 1, wherein the solid support is a bibulous material.

10. A device of claim 1, wherein the solid support is nitrocellulose.

11. A device of claim 1, wherein the solid support is a non-bibulous material.

12. A device of claim 1, wherein a predetermined concentration of analyte can be discerned from a signal ratio area when the signals from the first and second signal zones are approximately equal.

13. A device of claim 1, wherein the total amount of the first member of an inverse ligand-receptor pair in a population of particles is such that from one to three predetermined concentrations of an analyte can be discerned from a signal ratio area, the first concentration indicated when the ratio between the first and second signal zones is or approaches infinity, the second concentration when the ration between the first and second signal zone is approximately one, and the third concentration indicated when the ratio between the first and second signal zones is approximately the inverse of infinity.

* * * * *